United States Patent [19]
Leung et al.

[11] Patent Number: 6,077,990
[45] Date of Patent: Jun. 20, 2000

[54] PAR2 MODIFIED TRANSGENIC MICE

[75] Inventors: Wai-Ping Leung, San Diego, Calif.; Andrew Darrow, Lansdale; Patricia Andrade-Gordon, Doylestown, both of Pa.

[73] Assignee: Ortho-McNeil Pharmaceutical, Inc., Raritan, N.J.

[21] Appl. No.: 09/131,956

[22] Filed: Aug. 11, 1998

Related U.S. Application Data

[60] Provisional application No. 60/055,484, Aug. 12, 1997.

[51] Int. Cl.[7] .............................. C12N 5/00; C12N 15/00; C12N 15/09; C12N 15/63
[52] U.S. Cl. ................................. 800/18; 800/13; 800/21; 800/25; 435/325; 435/455; 435/461; 435/463
[58] Field of Search .................................. 800/13, 18, 21, 800/25; 435/325, 455, 461, 463

[56] References Cited

U.S. PATENT DOCUMENTS 5,175,384  12/1992  Krimpenfort et al. ...................... 800/2

OTHER PUBLICATIONS

Mullins et al., J. Clin. Invest., 98:S37–S40, 1996.

Seamark, R.F., Reprod. Fertil. Dev., 6:653–657, 1994.

Bradley et al., Bio/Technology, 10:534–539, 1992.

Capecchi, M.R., Scientific American, 270:34–41, 1994.

Nystedt et al., Proc. Natl. Acad. Sci. USA, 91:9208–9212, 1994.

*Primary Examiner*—Jasemine C. Chambers
*Assistant Examiner*—Janet M. Kerr
*Attorney, Agent, or Firm*—John W. Wallen

[57] ABSTRACT

Transgenic mice with a non-functional proteinase activated receptor-2 (PAR2) gene are prepared by targeted disruption of the endogenous PAR2 gene. The resulting transgenic mice display a phenotype including a lack of a hypotensive response to administration of the peptide, SLIGRL, and a reduction in carrageenin-induced paw edema compared to wild type mice.

5 Claims, 4 Drawing Sheets

PAR2 MODIFIED TRANSGENIC MICE

This application claims benefit of U.S. provisional application Ser. No. 60/055,484,filed Aug. 12, 1997.

FIELD OF THE INVENTION

The present invention relates to transgenic nonhuman animals wherein a PAR2 gene is altered, producing an animal lacking functional PAR2 protein.

BACKGROUND OF THE INVENTION

Protease activated receptor-2 (PAR-2) belongs to a new family of G protein-coupled receptors which are activated by proteolytic cleavage at the amino-terminus exposing a tethered ligand which binds to an as yet unidentified region of the receptor. In this study, we describe the development of a PAR-2 gene-disrupted mouse (−/−) by homologous recombination in embryonic stem cells, and demonstrate, for the first time, in vivo evidence of PAR-2 function. PAR-2 −/− mice appear normal and proceed to adulthood. PAR-2 deficiency was confirmed by Northern analyses of harvested tissues and cultured cells. Loss of receptor function was determined by the absence of the hypotensive response to an intravenous injection of the murine PAR-2 activating peptide, SLIGRI [SEQ. ID. NO:1]. Most interestingly, PAR-2 −/− mice had significantly less edema associated with carageenin induced paw inflammation. This report represents the first in vivo evidence that PAR-2 may play a role in the acute phase of the inflammatory response.

SUMMARY OF THE INVENTION

To understand the functional role of PAR2 in different cell types, mice that do not express the functional PAR2 were generated by homologous recombination (HR) in embryonic stem (ES) cells and are disclosed herein. These mice provide a valuable animal model to understand the function of PAR2 and to evaluate the therapeutic effects of drugs that modulate the function or the expression of PAR2 equivalents in human cells.

BRIEF DESCRIPTION OF THE DRAWINGS

FIGS. 1A–1C. Targeted disruption of the mouse PAR-2 gene.

FIGS. 2A–2B.

FIGS. 3A–3C. Arterial Pressure Responses to SLIGRL [SEQ. ID. NO:1]-NR$_2$, Angiotensin II and Acetylcholine in PAR-2+/+ and PAR-2 −/− Mice.

DETAILED DESCRIPTION OF THE INVENTION

The PAR2 knockout mice that were generated in the present invention provide a model in which the PAR2 gene was disrupted by homologous recombination (HR). The process of generating the knockout mice can be divided into 4 basic stages:

1. cloning of the PAR2 gene and preparation of DNA construct for transfection of embryonic stem (ES) cells;
2. isolating ES cells in which the PAR2 gene has been disrupted by HR;
3. generating chimeric mice from mouse embryos injected with the knockout ES cells; and
4. breeding chimeric mice to obtain knockout mice through germline transmission.

The present invention utilizes a cloned genomic DNA encoding the PAR2 protein and describes the cloning and characterization of the mouse PAR2 gene. Transgenic animals are generated which have altered the PAR2 gene. The alterations to the naturally occurring gene can be modifications, deletions and substitutions. Modifications and deletions render the naturally occurring gene nonfunctional, producing a "knockout" animal. Substitution of the naturally occurring gene for a gene from a second species results in an animal which produces the gene product of the second species. Substitution of the naturally occurring gene for a gene having a mutation results in an animal which produces the mutated gene product. These transgenic animals are critical for drug antagonist or agonist studies, the creation of animal models of human diseases, and for eventual treatment of disorders or diseases associated with PAR2-mediated responses. A transgenic animal carrying a "knockout" of PAR2 is useful for the establishment of a nonhuman model for diseases involving PAR2 equivalents in the human.

A transgenic mouse carrying the disrupted PAR2 gene was generated by homologous recombination of a target DNA construct with the endogenous gene in the chromosome. The DNA construct was prepared from a genomic clone of PAR2 which was isolated from a genomic DNA library.

The term "animal" is used herein to include all vertebrate animals, except humans. It also includes an individual animal in all stages of development, including embryonic and fetal stages. A "transgenic animal" is any animal containing one or more cells bearing genetic information altered or received, directly or indirectly, by deliberate genetic manipulation at a subcellular level, such as by targeted recombination or microinjection or infection with recombinant virus. The term "transgenic animal" is not intended to encompass classical cross-breeding or in vitro fertilization, but rather is meant to encompass animals in which one or more cells are altered by, or receive, a recombinant DNA molecule. This recombinant DNA molecule may be specifically targeted to a defined genetic locus, may be randomly integrated within a chromosome, or it may be extrachromosomally replicating DNA. The term "germ cell line transgenic animal" refers to a transgenic animal in which the genetic alteration or genetic information was introduced into a germ line cell, thereby conferring the ability to transfer the genetic information to offspring. If such offspring in fact possess some or all of that alteration of genetic information, they are transgenic animals as well.

The alteration or genetic information may be foreign to the species of animal to which the recipient belongs, or foreign only to the particular individual recipient, or may be genetic information already possessed by the recipient. In the last case, the altered or introduced gene may be expressed differently than the native gene, or not expressed at all.

The altered PAR2 gene generally should not fully encode the same PAR2 as native to the host animal, and its expression product should be altered to a minor or great degree, or absent altogether. However, it is conceivable that a more modestly modified PAR2 gene will fall within the scope of the present invention.

The genes used for altering a target gene may be obtained by a wide variety of techniques that include, but are not limited to, isolation from genomic sources, preparation of cDNAa from isolated mRNA templates, direct synthesis, or a combination thereof.

A type of target cell for transgene introduction is the embryonal stem cell (ES). ES cells may be obtained from preimplantation embryos cultured in vitro [M. J. Evans et al., Nature 292: 154–156 (1981); M. O. Bradley et al., Nature 309: 255–258 (1984); Gossler et al. Proc. Natl. Acad. Sci. USA 83: 9065–9069 (1986); Robertson et al., Nature 322, 445–448 (1986); S. A. Wood et al., Proc. Natl. Acad. Sci. USA 90: 4582–4584 (1993)]. Trangenes can be efficiently introduced into the ES cells by standard techniques such as DNA transfection or by retrovirus-mediated transduction. The resultant transformed ES cells can thereafter be combined with blastocysts from a nonhuman animal. The introduced ES cells thereafter colonize the embryo and contribute to the germ line of the resulting chimeric animal (R. Jaenisch, Science 240: 1468–1474 (1988)).

Since PAR2 is an independent component of a complex mechanism, the proteins, including that encoded by PAR2 DNA, must be examined both individually and as a group if their contribution to the mechanisms are to be understood. One approach to the problem of determining the contributions of individual genes and their expression products is to use isolated genes to selectively inactivate the native wild-type gene in totipotent ES cells (such as those described herein) and then generate transgenic mice. The use of gene-targeted ES cells in the generation of gene-targeted transgenic mice was described in 1987 (Thomas et al., Cell 51:503–512, (1987)) and is reviewed elsewhere (Frohman et al., Cell 56:145–147 (1989); Capecchi, Trends in Genet. 5:70–76 (1989); Baribault et al., Mol. Biol. Med. 6:481–492, (1989); Wagner, EMBO J. 9: 3025–3032 (1990); Bradley et al., Bio/Technology 10: 534–539 (1992)).

Techniques are available to inactivate or alter any genetic region to any mutation desired by using targeted homologous recombination to insert specific changes into chromosomal genes. Homologous recombination was reported to be detected at frequencies between $10^{-6}$ and $10^{-3}$ (Lin et al., Proc. Natl. Acad. Sci. USA 82:1391–1395 (1985); Smithies et al., Nature 317: 230–234 (1985); Thomas et al., Cell 44:419–428, (1986); Song et al., Proc Natl. Acad. Sci. USA 84:6820–6824 (1987)). Nonhomologous plasmid-chomosome interactions are more frequent, occurring at levels $10^5$-fold (Lin et al., Proc. Natl. Acad. Sci. USA 82:1391–1395 (1985)) to $10^2$-fold (Thomas et al., Cell 44:419–428 (1986); Song et al., Proc. Natl. Acad. Sci. USA 84:682–6824 (1987)) greater than comparable homologous insertion.

To overcome this low proportion of targeted recombination in murine ES cells, various strategies have been developed to detect or select rare homologous recombinants. One approach for detecting homologous alteration events uses the polymerase chain reaction (PCR) to screen pools of transformant cells for homologous insertion, followed by screening individual clones (Kim et al., Nucleic Acids Res. 16:8887–8903 (1988); Kim et al., Gene 103:227–233 (1991)). Alternatively, a positive genetic selection approach has been developed in which a marker gene is constructed which will only be active if homologous insertion occurs, allowing these recombinants to be selected directly (Sedivy et al., Proc. Natl. Acad. Sci. USA 86:227–231 (1989)). One of the most powerful approaches developed for selecting homologous recombinants is the positive-negative selection (PNS) method developed for genes (such as PAR2) for which no direct selection of the alteration exists (Mansour et al., Nature 336:348–352: (1988); Capecchi, Science 244:1288–1292, (1989); Capecchi, Trends in Genet. 5:70–76 (1989)). The PNS method is more efficient for targeting genes which are not expressed at high levels because the marker gene has its own promoter. Nonhomologous recombinants are selected against by using the Herpes Simplex virus thymidine kinase (HSV-TK) gene flanking the DNA construct. Cells with nonhomologous insertion of the construct express HSV thymidine kinase and therefore are sensitive to the herpes drugs such as gancyclovir (GANC) or FIAU (1-(2-deoxy 2-fluoro-B-D-arabinofluranosyl)-5-iodouracil). By this counter-section, the number of homologous recombinants in the surviving transformants can be increased.

As used herein, a "targeted gene" or "knockout" is a DNA sequence introduced into the germline of a non-human animal by way of human intervention, including but not limited to, the methods described herein. The targeted genes of the invention include DNA sequences which are designed to specifically alter cognate endogenouos genes.

All the above applications have to be verified in animal tests and eventually clinical trials. One approach to determine the functional role of the drug target is to study the defects resulting from the disrupted gene in a whole animal. The PAR2 knockout mice that have been generated and are disclosed herein will allow the definition of the function of PAR2 which is critical in deciding the types of modulators are most suitable in therapies.

Any PAR2 function that is detected in the knockout mice of the present invention would provide evidence of the existence of alternative novel PAR2 subtypes which may then be isolated from the knockout mice of the present invention.

The absence of functional PAR2 in the knockout mice of the present invention are confirmed in RNA analysis, protein expression detection, receptor binding assays and other receptor functional studies. For RNA analysis, RNA samples are prepared from different organs of the knockout mice and the PAR2 transcript are detected in Northern blots using oligonucleotide probes specific for the transcript.

Polyserum and monoclonal antibodies that are specific for the mouse PAR2 are produced. The absence of intact PAR2 in the knockout mice are studied in flow cytometric analysis, in immunohistochemical staining, and in receptor binding assays using PAR2-specific antibodies. Alternatively, functional assays are performed using preparations of different cell types collected from the knockout mice.

The following examples are presented for the purpose of illustrating the present invention and are not to be construed as a limitation on the scope of this invention.

EXAMPLE 1

Protease activated receptor 2(PAR-2) is a G-protein coupled receptor, which like the thrombin receptor (PAR-1), is activated by proteolytic cleavage of the amino-terminus, exposing a tethered-peptide ligand (1,2). As with the ThrR, a synthetic hexapeptide representing the first six amino acids following the putative cleavage-site (SLIGRL [SEQ. ID. NO:1] in the murine form, SLIGKV [SEQ. ID. NO.:2] in the human form) is an agonist for PAR-2 activation (2,3). Tissue distribution studies show high expression of PAR-2 mRNA in vascularized tissues and the gastrointestinal tract (1). Functional PAR-2 was first described in vitro in human epidermal keratinocytes (4) and has subsequently been described in Jurkat T cells (5), human umbilical vein endothelial cells (6), human intestinal epithelial cells (7), epithelial-derived tumor cell lines (7), rat gastric tissue (8), pancreatic acinar cells (8) and rat porcine vascular tissue (9,10). Our laboratories have further identified PAR-2 expression in rat CNS-derived cells, murine lung myofibroblasts, and murine intestinal and vascular smooth muscle (11).

The physiological activating protease for PAR-2 has not been identified. Trypsin, but not thrombin, cleaves PAR-2 to its active form and may in fact act as the endogenous ligand in the gastrointestinal tract. Recent studies have indicated that mast cell tryptase activates PAR-2 in endothelial cells and in cells transfected with PAR-2 (12). Mast cells have been implicated in the inflammatory reactions of airways, skin, and intestine (13). Furthermore, mast cell tryptase has been shown to regulate neurogenic inflammation in the skin (14). The tissue distribution and possible activation by tryptase of PAR-2 have elicited hypotheses for the role of PAR-2 in areas of tissue repair and inflammation. However, experimental evidence for tryptase acting as a physiological protease activator has not been demonstrated thus far.

Figure 1A:
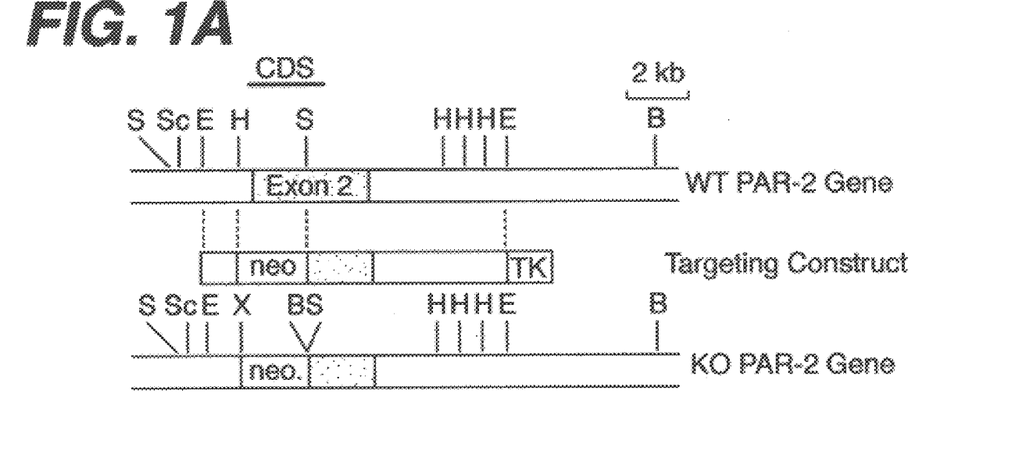
FIG. 1A: The map shows the organization of part of the PAR-2 gene before (top) and after (bottom) homologous recombination with the targeting construct (middle). A 1.8 kb HindIII-SalI region which covers part of intron 1 and exon 2 (cds represents coding sequence) was deleted and replaced with the neomycin resistance gene (neo). The thymidine kinase gene cassette (TK) was placed 3' flanking the construct (Ref 1). Exons are shown as solid boxes. Restriction sites are BamHI (B), EcoRI (E), HindIII (H), SalI (S), ScaI (Sc) and XhoI (X).

To elucidate the potential functions of this unique receptor, a PAR-2 gene-disrupted mouse was developed by homologous recombination in embryonic stem cells. The murine PAR-2 gene was cloned from mouse genomic DNA and characterized (15). A targeting vector was constructed in which a 1.8 kb region of intron 1 and exon 2 was deleted and replaced with the insertion of the neomycin resistant gene (FIG. 1A). This deletion resulted in the removal of 309 amino acids including the protease cleavage site of the amino terminus up to transmembrane domain 7 of the receptor.

Figure 1B:
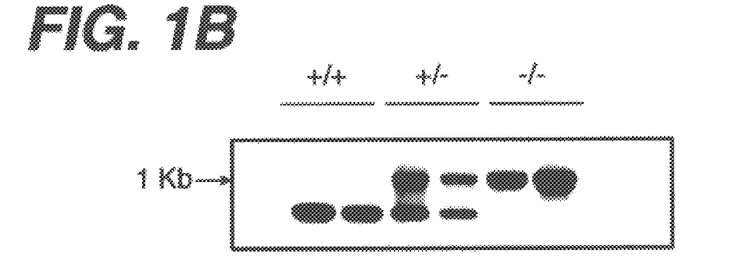
FIG. 1B: PCR analyses of tail DNA from pups resulting from PAR-2 +/− matings.

Matings of heterozygous pairs of mice were carried out through 4 cycles. Mice were genotyped by PCR analyses (26) of DNA prepared from tail snips (FIG. 1B). Litter size ranged from 6–12 offspring. Of 419 mice analyzed, 28.4% were wild type (+/+), 54.9% were heterozygous (+/−), and 16.7% were homozygous (−/−) which represents a significant variation (p<0.005) from the expected Mendelian ratio (25:50:25). Furthermore, 20.0% of all PAR-2 −/− mice were either still born or found dead within 48 hours of birth in comparison to 8.4% and 6.4% of PAR-2 +/+ and +/− mice respectively (p<0.005). Five pups from each genotype, which died within 48 hours of birth, were analyzed for anatomical and histological defects. No abnormalities were observed in any of these mice. We postulate that the postnasal mortality may be associated with poor maternal care. The remaining animals proceeded to maturity apparently without incident. Surviving PAR-2 −/− mice appeared normal upon gross anatomical and histological analysis. In addition, mating of PAR-2 −/− males with PAR-2 −/− females resulted in normal litter size and offspring.

Figure 1C:
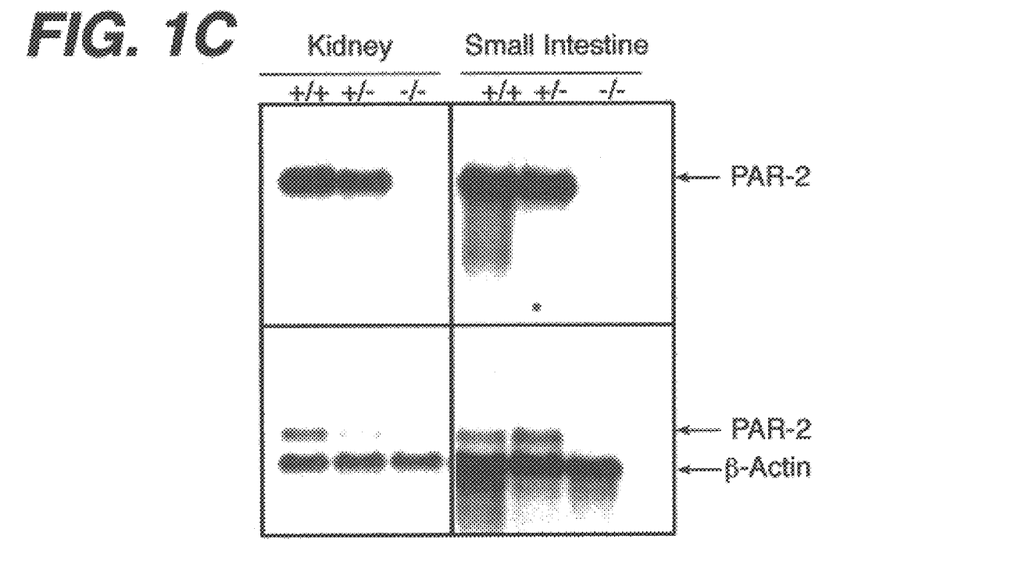
FIG. 1C: Northern Analyses of poly A+RNA from kidney and small intestine indicating absence of PAR-2 RNA in tissue from −/− mice.
Figure 2A:
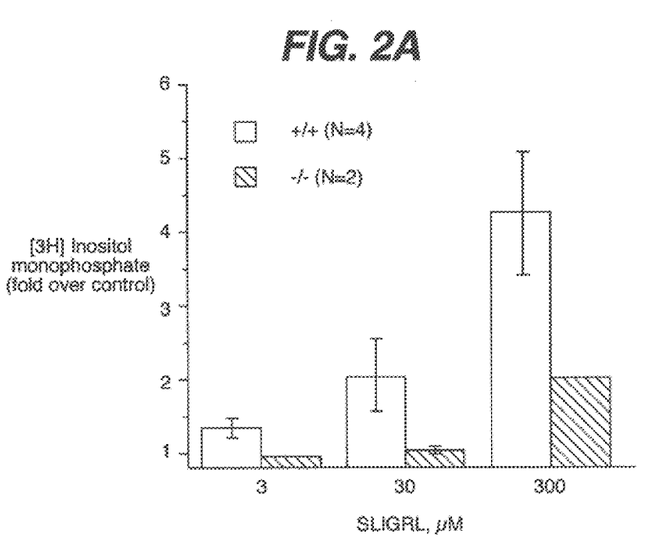
FIG. 2A: PAR-2-dependent [$^3$H]inositol monophosphate formation in +/+ and −/− lung cells. Cells were stimulated with SLIGRL [SEQ. ID. NO:1]-NH$_2$ at 3, 30 and 300 µM. Results represent the mean±sem from four and two independent cultures for PAR-2 +/+ and −/− mice, respectively.
Figure 2B:
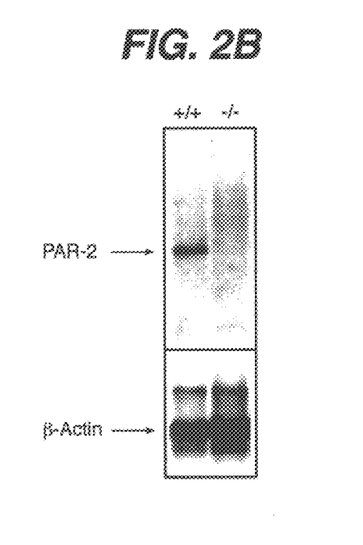
FIG. 2B: Northern analysis of PAR-2 expression in RNA prepared from lung cell cultures from PAR-2 +/+ and −/− mice.

Northern blot analysis (17) confirmed the total ablation of the PAR-2 transcript in PAR-2 −/− mice (FIG. 1C). Poly A+ mRNA was prepared from kidney and intestine of adult PAR-2 +/+, +/−, and −/− mice. Lung tissue was harvested from PAR-2 +/+ and −/− mice to establish cell cultures for determination of less of PAR-2 function in these cells (18). SLIGRL [SEQ. ID. NO.:1]-induced inositol monophosphate formation was reduced, but not absent in PAR-2 −/− derived cells in comparison to PAR-2 +/+ cells (FIG. 2A). The absence of PAR-2 RNA in the cultures derived from PAR-2 −/− mice was validated by Northern blot analyses (FIG. 2B). Cells from both PAR-2 −/− and +/+ mice did not respond to a scrambled control peptide, LSIGRL, but demonstrated strong responses to the mitogen, PDGF BB (results not shown). The capacity of SLIGRL [SEQ. ID. NO.:1] to activate cells from PAR-2 −/− mice is not clear but may be due to cross-activation of SLIGRL [SEQ. ID. NO.:1] with another PAR-2 like receptor or activation of a peptide sensitive element.

Figure 3A:
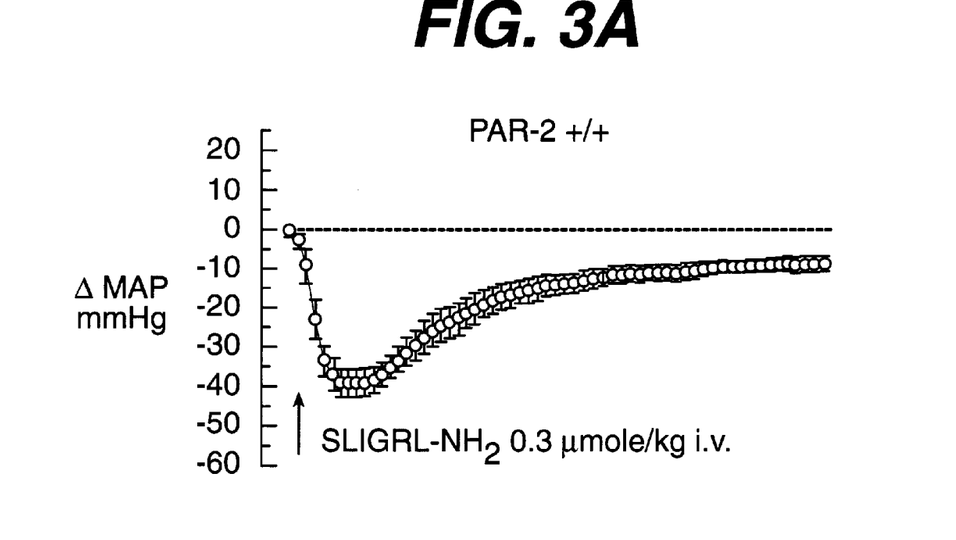
FIGS. 3A and 3B demonstrate the arterial pressure response (mean change in MAP±sem) to SLIGRL-NH$_2$, 0.3 umole/kg i.v., in PAR$^{+/-}$ (n=4) and PAR$^{-/-}$ (n=3) mice, respectively.
Figure 3B:
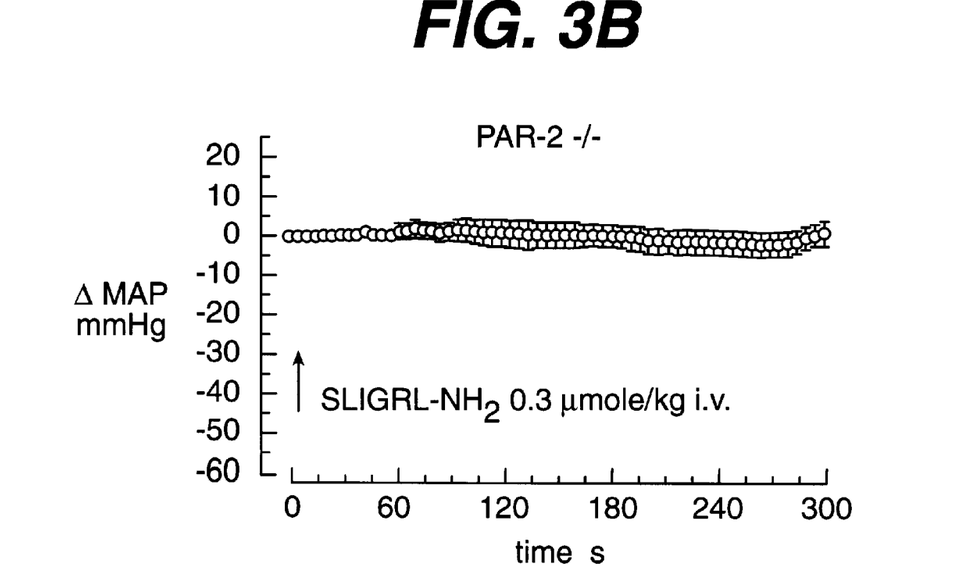
Figure 3C:
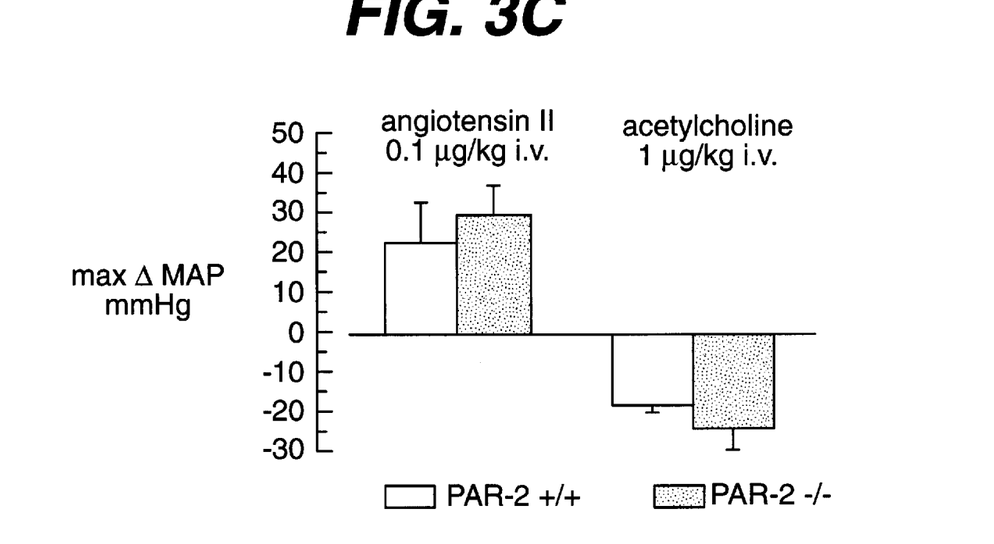
FIG. 3C summarizes the maximal arterial pressure changes induced by angiotensin II (0.1 µg/kg i.v.) and acetylcholine (1 µg/kg i.v.) in PAR-2 +/+ and PAR-2 −/− mice.
Figure 4:
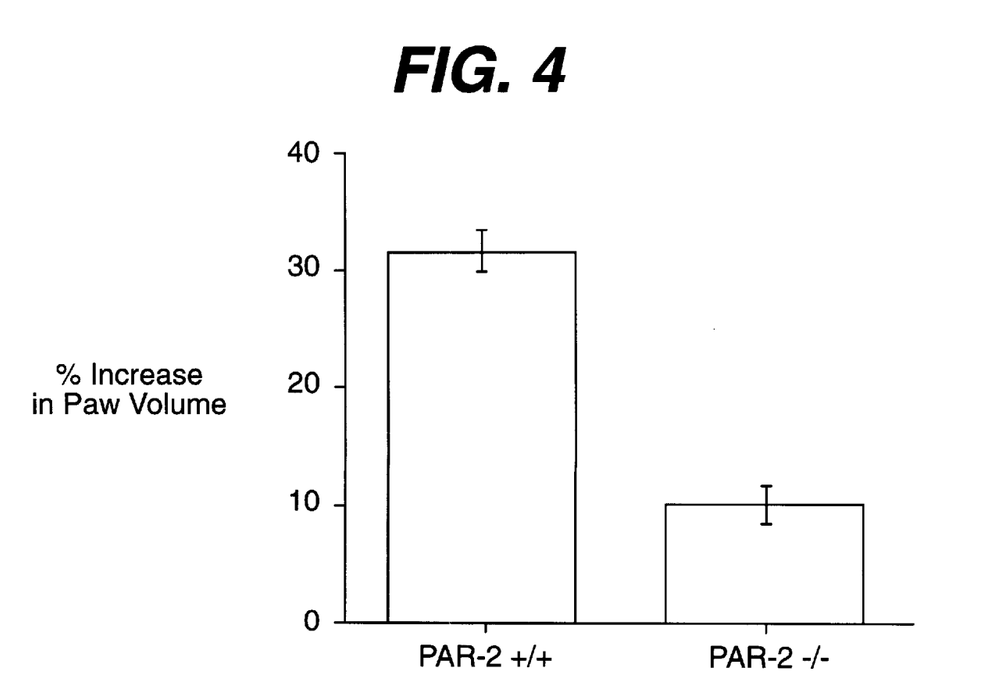
FIG. 4. Percent increase in paw volume in PAR-2 +/+ and −/− mice 60 min following a subplantar injection of 25 µl of a 2% lambda carrageenan solution.

In vivo loss of PAR-2 function was demonstrated by monitoring hemodynamic parameters in PAR-2 +/+ and −/− mice (19). Heart rate (HR) and mean arterial pressure (MAP) of PAR-2 +/+ and PAR-2 −/− mice were not significantly different: HR=514±16 and 445±45 beats/min, MAP= 96±4 and 88±8 mmHg in PAR-2 +/+ and PAR-2 −/− mice, respectively. Thus, PAR-2 does not appear to be involved in maintenance of normal arterial pressure. SLIGRL [SEQ. ID. NO.:1] has been shown to induce vasodilation in isolated vascular rings (20) and decrease arterial pressure following intravenous administration in anesthetized rats (10) and mice (21). The hypotensive response to intravenous SLIGRL [SEQ. ID. NO.:1] in PAR-2 +/+ mice (FIG. 3A) is consistent with these previous studies. In contrast, intravenous SLIGRL [SEQ. ID. NO.:1] had no effect on MAP in PAR-2 −/− mice (FIG. 3B) confirming loss of PAR-2 function. The hypertensive response to angiotensin II and the hypotensive response to acetylcholine were similar in PAR-2 +/+ and PAR-2 −/− mice (FIG. 3C). Therefore, the hypotensive action of PAR-2 is not involved in the maintenance of basal arterial pressure or in the response to other vasoactive stimuli. Moreover, thrombin receptor activation with SFLLRN [SEQ. ID. NO.:3] which also induces changes in arterial pressure (10,22) produced comparable arterial pressure responses in PAR-2 +/+ and PAR-2 −/− mice (data not shown). Thus, both in vitro and vivo studies have confirmed the absence of PAR-2 function in PAR-2 −/− mice.

The lack of knowledge for the protease responsible for PAR-2 activation and the absence of receptor antagonists have limited the possibilities to study the function of PAR-2 in normal and pathophysiologic states. The availability of PAR-2 −/− mice provides a valuable tool for evaluating the role of PAR-2 in various disease conditions. The identification of PAR-2 on endothelial cells suggests that PAR-2 may participate in cellular responses associated with the acute phase of inflammation, including vasodilation, increased vascular permeability leading to edema and leukocyte migration; processes known to involve endothelial activation. The ability of SLIGRL [SEQ. ID. NO.:1] to induce endothelial dependent vasodilation in vivo suggests that activation of PAR-2, by an as yet known protease, may play a role in mediating inflammatory responses. To investigate the role of PAR-2 in the acute phase of inflammation, PAR-2 +/+ and −/− mice were evaluated in a carageenin-induced paw edema model (23). At 60 min post carageenin injection, paw volume increased in PAR-2 +/+ mice, as expected. In contrast, the increase in PAW volume observed in PAR-2 −/− mice was significantly reduced and represented approximately a 68% reduction in the inflammatory response (p<0.005). This represents the first in vivo evidence demonstrating the potential role of PAR-2 in inflammation and raises the possibility that modulation of PAR-2 directly, or indirectly via its endogenous enzymatic activator, may provide therapeutic benefit in acute and chronic inflammatory diseases.

Both the absence of vasodilating (hypotensive) response to SLIGRL [SEQ. ID. NO.:1] and the reduced carageenin-induced paw edema in PAR-2 −/− mice provide direct in vivo evidence for a role for PAR-2 in the acute phase of an inflammatory response. Previous in vitro studies have indicated that PAR-2 expression is increased in human endothelial cells by the inflammatory mediators, interleukin-1, fumor necrosis factor α, and lipopolysaccharide, thus providing a mechanism for amplifying the response to proteases that activate PAR-2. These mediators are known to participate on processes associated with leukocyte adhesion and emigration into sites of injury.

The results presented in this study provide the first in vivo evidence demonstrating the potential role for PAR-2 in inflammation and raises the possibility that modulation of PAR-2 either directly, or indirectly, via its endogenous enzymatic activator, may provide therapeutic benefit in acute and chronic inflammatory diseases. The mounting in vitro and in vivo evidence suggests that PAR-2 may play a broad role in mediating inflammation-associated events both at late and early stages. Determination of the precise role of PAR-2 in inflammation will require further investigation, including the identification of the physiological activator of PAR-2 as well as its presence at sites of inflammation.

REFERENCES

1. T. K. H. Vu, D. T. Hung, V. I. Wheaton, S. R. Couglin, *Cell* 64, 1057 (1991).

2. S. Nystedt, K. Emilsson, C. Wahlestedt, J. Sundelin, *Proc. Natl. Acad. Sci. USA* 91, 9208 (1994).

3. S. Nystedt, K. Emilsson, A. K. Larsson, B. Strombeck, J. Sundelin, *Eur. J. Biochem.* 232,84 (1995).

4. R. S. Santulli, C. K. Derian, A. L. Darrow, K. A. Tomko, A. J. Eckardt, M. Seiberg, R. M. Scarborough, P. Andrede-Gordon, *Proc. Natl. Acad. Sci. USA* 92, 915 (1995).

5. B. Mari, S. Guerin, D. Farahi Far, J. P. Breitmayer, N. Belhacene, J. F. Peyron, B. Rossi, P. Auberger, P. *FASEB J.* 10, 309 (1996).

6. H. Mirza, V. Yatsula, W. F. Bahou, *J. Clin. Invest.* 97, 1705 (1996).

7. S. K. Bohm, W. Kong, D. Bromme, S. P. Smeekens, D. C. Anderson, A. Connolly, M. Kahn, N. A. Nelken, S. R. Coughlin, D. G. Payan, N. W. Bunnett, *Biochem. J.* 314, 1009 (1996).

8. M. Saifeddine, B. Al-Ani, C. H. Cheng, L. Wang, M. D. Hollenberg, *Brit. J. Pharmacol.* 118, 521 (1996).

9. M. D. Hollerberg, M. Saifeddine, B. Al-Ani, *Mol. Pharmacol.* 49, 229 (1996).

10. J. J. Hwa, L. Ghibaudi, P. Williams, M. Chintala, R. Zhang, M. Chatterjee, E. Sybertz, *Circ. Res.* 78, 581 (1996).

11. M. D'Angrea, D. LeTurq, C. Derian, V. Smith-Swintosky, A. Darrow, R. Santulli, P. Andrade-Gordon. unpublished results.

12. M. Molino, E. S. Barnathan, B. Numerof, J. Clark, M. Dreyer, A. Cumashi, J. Hoxie, N. Schecter, M. Woodkalis, L. F. Brass, *J. Biol. Chem.* in press, (1997).

13. J. S. Marshall, J. Bienenstock, *Cur. Opin. Immunol.* 6, 853 (1994).

14. A. Naukkarinen, I. T. Harvima, M. L. Aalto, M. Horsmanheimo, *Int. J. Dermatol.* 33, 361 (1994).

15. A 129/SV mouse genomic DNA fragment (~14 kb) containing the PAR-2 gene was cloned and characterized by restriction mapping. A 1.3 kb EcoRI-HindIII fragment of the PAR-2 gene was prepared by PCR using oligonucleotides 5'-GCATA CACATCTGCAGACCAG-3' [SEQ. ID. NO.:4] and 5'-GCTGGTCTCAGATTCCTTAAG-3' [SEQ. ID. NO.:5]. This PCR fragment, used as a short homologous region, was placed 5' of the neomycin resistant gene cassette in the targeting construct. A 5.5 kb SalI-EcoRI DNA fragment covering part of exon 2 and the 3' flanking region of the PAR-2 gene was placed 3' of the neo cassette (FIG. 1). A HSV thymidine kinase (TK) gene cassette was also placed at the 3' end of the construct for negative selection. The construct DNA was introduced into E14 embryonic stem (ES) cells by electroporation and cultured in the presence of 400 µg/ml G418 and 0.2 µM ganciclovir (24). ES cells with the targeted gene were detected by PCR using the PAR-2 gene-specific oligonucleotide 5'-GTCCTCTTAACCGATGAGC CCTCTC-3' [SEQ. ID. NO.:6] and the neo-specific oligonucleotide 5'-TACCCGGTAGAATTGA CCTGCAG-3'[SEQ. ID. NO.:7]. After homologous recombination in the ES cells, the targeting construct led to a 1.8 kb deletion in the PAR-2 gene which resulted in the removal of 309 amino acids including the protease cleavage site and transmembrane domains from domain 1 up to part of domain 7 of the PAR-2 protein.

16. Tail DNA was prepared from 2–5 cm tail snips. PCR primers were designed with the assistance of the DNAstar Primer Design program. The following three primers (5'0-3') were used: mPAR-2 wild type (WT) upper, CTTGTCGC-CCTCTGCCTGTCG [SEQ. ID. NO.:8]; mPAR-2 WT lower, GCCACTGTTAGCCGGTTAGGATGC [SEQ. ID. NO.:9]; AND mPAR-2 NEO upper, GTGGGGGTGGGGTGGGATTAGATA [SEQ. ID. NO.:10]. The neo specific amplimer pair (mPAR-2 NEO upper+mPAR-2 WT lower) should yield a 1080 bp product in those DNA samples containing the NEO specific construct (PAR-2 +/− and −/− mice). The wild type specific amplimer pair (mPAR-2 WT upper+mPAR-2 WT lower) should yield a 760 bp product in those DNA samples from PAR-2 +/+ or +/− mice, a host start PCR procedure using 2 µl tail DNA, 250 nM of each primer, 40 mM dNTP mix, 3.5 Units Taq Plus polymerase (Strategene) and 5 µl was carried out on each sample. An Ampliwax PCR Gem 100 bead (Perkin Elmer) was placed in each tube, and reactions were heated at 80° C. for 5 min prior to addition of the Taq long polymerase (Stratagene). The following PCR conditions were employed: 2 cycles of 94° C.×1 min+65° C.×1 min+72° C.×2 min; 36 cycles of 94° C.×15 sec+65° C.×40 sec+72° C.×1.5 min; 1 cycle of 72° C.×2 min.

17. RNA was extracted from kidney and small intestine of +/+, +/− and −/− ThrR mice and from lung cell cultures from PAR-2 −/− and +/+ mice using Trizol (Gibco/BRL, Gaithersburg, Md.). Poly A selection with biotinylated oligo dT and Streptavidin MagneSphere paramagnetic particles (Promega, Madison, Wis.) was carried out in combination with a magnetic particle concentrator (Dynal, Lake Success, N.Y.). Northern gel electrophoresis, transfer, and blot hybridizations were performed by established procedures (25). A 452 bp PAR-2 probe (4) corresponds to nucleotides 154 to 585 of the murine PAR-2 coding sequence (26). All probes were radiolabeled by random primer incorporation of $^{32}$P dCTP (Gibco/BRL). Northern blots were subsequently probed by using human β-actin sequences (Clontech, Palo Alto, Calif.) for normalization. Following hybridization, the blots were washed at 60° C. twice in 2×SSC/0.1%SDS and twice in 0.5×SSC/0.1%SDS for 20 min/wash. Exposures were for four days with intensifying screens.

18. Lung tissue was removed, minced and digested with 4 mg/ml type I collagenase (Worthington). Cell suspensions were washed twice and seeded in 75 cm$^2$ flasks in DMEM containing 15% heat-inactivated FBS and antibiotics. Non-adherent cells were removed by washing at 24 h. At 70% confluence, cells were trypsinized and plated at 5×10$^4$ cells/well in 12-well cluster dishes. Measurement of [$^3$H] inositol monophosphate formation was performed as previously described (4) with the exception that cells were radiolabeled for 24 h in inositol-free DMEM.

19. Male mice, at least 4-months old and weighing 30–35 g, were ventilated with a gas mixture of isoflurane (0.75%), oxygen (95%), and carbon dioxide (5%) at 140 breaths/min and a tidal volume of 0.2 ml, using a rodent respirator. Body temperature was maintained at 38° C. with a heating lamp and a proportional temperature controller. Subdermal needle electrodes were inserted for recording lead II electrocardiogram (ECG). A length of Teflon AWG30 tubing, tapered at one end, was filled with heparin (10 U/ml) and inserted into the right carotid artery, advanced to the thoracic aorta and attached to a Statham P50 pressure transducer (Spectramed, Oxnard, Calif.) for recording arterial blood pressure. Mico-Renthane® MRE-033 (Braintree Scientific, Inc., Braintree, Mass.) tubing was inserted into the right jugular vein for administration of drugs. All hemodynamic and ECG measurements were recorded and analyzed with a digital data acquisition system (HD5/16/SW, Po-Ne-Mah, Simsbury, Conn.). Blood pressure and ECG were continuously monitored during the study. Animals were allowed to stabilize for at least 30–60 min. SLIGRL [SEQ. ID. NO.:1]-NH$_2$, SFLLRN [SEQ. ID. NO.:5]-NH$_2$, LSIGRL [SEQ. ID. NO.:11]-NH$_2$, angiotensin II and acetylcholine were dissolved in saline at the appropriate concentrations. Following control measurements, SLIGRL [SEQ. ID. NO.:1]-NH$_2$ (0.3 μmole/kg), SFLLRN [SEQ. ID. NO.: 3]-NH$_2$ (0.3 μmole/kg) or LSIGRL [SEQ. ID. NO.:11]-NH$_2$ (1 μmole/kg) was infused intravenously as a bolus in a 4 μl volume. Hemodynamic parameters were monitored for 10 min after each dose. Twenty to 30 min after administration of peptides, the responses to angiotensin II (0.1 μg/kg) and acetylcholine (1 μg/kg) were evaluated.

20. B. Al-Ani, M. Saifeddine, M. D. Hollenberg, *Can. J. Physiol. Pharmacol.* 73, 1203 (1995).

21. W. Cheung, P. Andrade Gordon, C. K. Derian, B. P. Damiano, *Circulation* 94:1588 (1996). Abstract.

22. S. Nystedt, V. Ramakrishnan, J. Sundelin, *J. Biol. Chem.* 271, 14910 (1996).

23. Under brief methoxyflurane anesthesia, 25 μl of 2% lambda carrageenan (Sigma, St. Louis, Mo.) dissolved in saline was injected into the subplantar space of the right, rear paw of PAR-2 +/+ and –/– mice. Paw volume was measured before and 60 min after injection using an automated mercury plethysmometer (Buxco, Inc., Conn.). Studies were performed blinded.

24. W. P. Fung-Leung, T. M. Kundig, K. Ngo, J. Panakos, J. De Sousa-Hitzler, E. Wang, P. S. Ohashi, T. W. Mak, C. Y. Lau *J. Exp. Med.* 180, 959 (1994).

25. J. Sambrook, E. F. Fritsch, T. Maniatis, *Molecular Cloning: A Laboratory Manual,* 2nd edit., Cold Spring Harbor Laboratory Press, Cold Spring Harbor, N.Y. (1989).

26. S. Nystedt, A. K. Larsson, H. Aberg, and J. Sundelin, *J. Biol. Chem.* 270, 5950 (1996).

---

What is claimed is:

1. A transgenic mouse whose somatic and germ cells comprise a disruption in an endogenous proteinase activated receptor 2 (PAR2) gene, wherein disruption said is generated by targeted replacement with a non-functional PAR2 gene, and wherein said disruption results in said mouse having a lack of hypotensive response to administration of the amino acid sequence SLIGRL (SEQ. ID. NO.1) and a reduction in carageenin-induced paw edema as compared to wild-type PAR2 mice.

2. The mouse of claim 1, wherein said mouse is fertile and transmits the non-functional PAR2 gene to its offspring.

3. The mouse of claim 1, wherein the non-functional PAR2 gene has been introduced into an ancestor of the mouse at an embryonic stage by microinjection of an embryonic stem cell.

4. A method for producing a transgenic mouse whose somatic and germ cells comprise a disruption in an endogenous PAR2 gene, wherein said disruption is generated by targeted replacement with a non-functional PAR2 gene, said method comprising:

(a) introducing a PAR2 gene targeting construct comprising a selectable marker sequence into a mouse embryonic stem cell;

(b) introducing said mouse embryonic stem cell into a mouse blastocyst;

(c) transplanting said blastocyst into a pseudopregnant mouse;

(d) allowing said blastocyst to develop to term;

(e) identifying a transgenic mouse whose genome comprises a disruption of an endogenous PAR2 gene in at least one allele; and (f) breeding the transgenic mouse identified in step (e) to obtain a transgenic mouse whose genome comprises a homozygous disruption of the endogenous PAR2 gene, wherein said disruption results in said mouse having a lack of hypotensive response to administration of the amino acid sequence (SEQ. ID. NO.1) and a reduction in carageenin-induced paw edema as compared to wild-type PAR2 mice.

5. The method of claim 4 wherein the introducing of step (a) is by electroporation or microinjection.

* * * * *

SEQUENCE LISTING (1) GENERAL INFORMATION:

(iii) NUMBER OF SEQUENCES: 11

(2) INFORMATION FOR SEQ ID NO:1:

(i) SEQUENCE CHARACTERISTICS:
        (A) LENGTH: 6 amino acids
        (B) TYPE: amino acid
        (C) STRANDEDNESS: single
        (D) TOPOLOGY: linear     (ii) MOLECULE TYPE: peptide     (iv) ANTI-SENSE: NO     (xi) SEQUENCE DESCRIPTION: SEQ ID NO:1:

Ser Leu Ile Gly Arg Leu
1             5

(2) INFORMATION FOR SEQ ID NO:2:

(i) SEQUENCE CHARACTERISTICS:
        (A) LENGTH: 6 amino acids (B) TYPE: amino acid
        (C) STRANDEDNESS: single
        (D) TOPOLOGY: linear (ii) MOLECULE TYPE: peptide (iv) ANTI-SENSE: NO (xi) SEQUENCE DESCRIPTION: SEQ ID NO:2:

Ser Leu Ile Gly Lys Val
1               5

(2) INFORMATION FOR SEQ ID NO:3:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (iv) ANTI-SENSE: NO (xi) SEQUENCE DESCRIPTION: SEQ ID NO:3:

Ser Phe Leu Leu Arg Asn
1               5

(2) INFORMATION FOR SEQ ID NO:4:

(i) SEQUENCE CHARACTERISTICS:
        (A) LENGTH: 21 base pairs
        (B) TYPE: nucleic acid
        (C) STRANDEDNESS: double
        (D) TOPOLOGY: linear (ii) MOLECULE TYPE: cDNA (iv) ANTI-SENSE: NO (xi) SEQUENCE DESCRIPTION: SEQ ID NO:4:

GCATACACAT CTGCAGACCA G                                             21

(2) INFORMATION FOR SEQ ID NO:5:

(i) SEQUENCE CHARACTERISTICS:
        (A) LENGTH: 21 base pairs
        (B) TYPE: nucleic acid
        (C) STRANDEDNESS: double
        (D) TOPOLOGY: linear (ii) MOLECULE TYPE: cDNA (iv) ANTI-SENSE: NO (xi) SEQUENCE DESCRIPTION: SEQ ID NO:5:

GCTGGTCTCA GATTCCTTAA G                                             21

(2) INFORMATION FOR SEQ ID NO:6:

(i) SEQUENCE CHARACTERISTICS:
        (A) LENGTH: 25 base pairs
        (B) TYPE: nucleic acid
        (C) STRANDEDNESS: double
        (D) TOPOLOGY: linear (ii) MOLECULE TYPE: cDNA (iv) ANTI-SENSE: NO (xi) SEQUENCE DESCRIPTION: SEQ ID NO:6:

GTCCTCTTAA CCGATGAGCC CTCTC                                              25

(2) INFORMATION FOR SEQ ID NO:7:

(i) SEQUENCE CHARACTERISTICS:
        (A) LENGTH: 23 base pairs
        (B) TYPE: nucleic acid
        (C) STRANDEDNESS: double
        (D) TOPOLOGY: linear (ii) MOLECULE TYPE: cDNA (iv) ANTI-SENSE: NO (xi) SEQUENCE DESCRIPTION: SEQ ID NO:7:

TACCCGGTAG AATTGACCTG CAG                                                23

(2) INFORMATION FOR SEQ ID NO:8:

(i) SEQUENCE CHARACTERISTICS:
        (A) LENGTH: 21 base pairs
        (B) TYPE: nucleic acid
        (C) STRANDEDNESS: double
        (D) TOPOLOGY: linear (ii) MOLECULE TYPE: cDNA (iv) ANTI-SENSE: NO (xi) SEQUENCE DESCRIPTION: SEQ ID NO:8:

CTTGTCGCCC TCTGCCTGTC G                                                  21

(2) INFORMATION FOR SEQ ID NO:9:

(i) SEQUENCE CHARACTERISTICS:
        (A) LENGTH: 24 base pairs
        (B) TYPE: nucleic acid
        (C) STRANDEDNESS: double
        (D) TOPOLOGY: linear (ii) MOLECULE TYPE: cDNA (iv) ANTI-SENSE: NO (xi) SEQUENCE DESCRIPTION: SEQ ID NO:9:

GCCACTGTTA GCCGGTTAGG ATGC                                               24

(2) INFORMATION FOR SEQ ID NO:10:

(i) SEQUENCE CHARACTERISTICS:
        (A) LENGTH: 24 base pairs
        (B) TYPE: nucleic acid
        (C) STRANDEDNESS: double
        (D) TOPOLOGY: linear (ii) MOLECULE TYPE: cDNA (iv) ANTI-SENSE: NO (xi) SEQUENCE DESCRIPTION: SEQ ID NO:10:

GTGGGGGTGG GGTGGGATTA GATA                                               24

(2) INFORMATION FOR SEQ ID NO:11:

(i) SEQUENCE CHARACTERISTICS:
        (A) LENGTH: 6 amino acids
        (B) TYPE: amino acid
        (C) STRANDEDNESS: single
        (D) TOPOLOGY: linear

```
        (ii) MOLECULE TYPE: peptide (iv) ANTI-SENSE: NO (xi) SEQUENCE DESCRIPTION: SEQ ID NO:11:

Leu Ser Ile Gly Arg Leu
1               5
```